US012465531B2

(12) United States Patent
Sasaki

(10) Patent No.: US 12,465,531 B2
(45) Date of Patent: Nov. 11, 2025

(54) UNDERPANTS-TYPE DISPOSABLE WEARING ARTICLE

(71) Applicant: DAIO PAPER CORPORATION, Ehime (JP)

(72) Inventor: Akane Sasaki, Tochigi (JP)

(73) Assignee: Daio Paper Corporation, Ehime (JP)

( * ) Notice: Subject to any disclaimer, the term of this patent is extended or adjusted under 35 U.S.C. 154(b) by 315 days.

(21) Appl. No.: 18/265,130

(22) PCT Filed: Jan. 14, 2022

(86) PCT No.: PCT/JP2022/001052

§ 371 (c)(1),
(2) Date: Jun. 2, 2023

(87) PCT Pub. No.: WO2022/185733

PCT Pub. Date: Sep. 9, 2022

(65) Prior Publication Data

US 2024/0000629 A1 Jan. 4, 2024

(30) Foreign Application Priority Data

Mar. 2, 2021 (JP) ................................ 2021-032655

(51) Int. Cl.
*A61F 13/494* (2006.01)
*A61F 13/496* (2006.01)

(52) U.S. Cl.
CPC .... *A61F 13/49466* (2013.01); *A61F 13/4963* (2013.01); *A61F 2013/4948* (2013.01)

(58) Field of Classification Search
CPC ............ A61F 13/49466; A61F 13/4963; A61F 2013/4948; A61F 13/4752; A61F 13/49012
See application file for complete search history.

(56) References Cited

U.S. PATENT DOCUMENTS

2015/0011958 A1 1/2015 Yoshioka
2018/0055698 A1* 3/2018 Bishop .................. A61F 13/496

FOREIGN PATENT DOCUMENTS

| | | |
|---|---|---|
| JP | H04-028363 | 1/1992 |
| JP | 08-154971 | 6/1996 |
| JP | H11-332913 | 12/1999 |
| JP | 2001-252303 | 9/2001 |
| JP | 2002-035029 | 2/2002 |
| JP | 2002-178428 | 6/2002 |
| JP | 2002-273808 | 9/2002 |
| JP | 2013-075106 | 4/2013 |
| JP | 2019-084414 | 6/2019 |
| JP | 2020-089682 | 6/2020 |
| WO | 2018/199918 | 11/2018 |

OTHER PUBLICATIONS

International Search Report and the Written Opinion for PCT/JP2022/001052, dated Mar. 29, 2022.

* cited by examiner

*Primary Examiner* — Susan S Su
*Assistant Examiner* — Erin A Kim
(74) *Attorney, Agent, or Firm* — Andrus Intellectual Property Law, LLP

(57) ABSTRACT

A dorsal side barrier is configured so as to stand up unintentionally when a diaper is used. This problem is solved by an underpants-type disposable diaper characterized by being provided with the dorsal side barrier which is unfolded so as to spread in a natural length state and which is turned up automatically when the diaper is stretched.

11 Claims, 16 Drawing Sheets

[FIG.1]
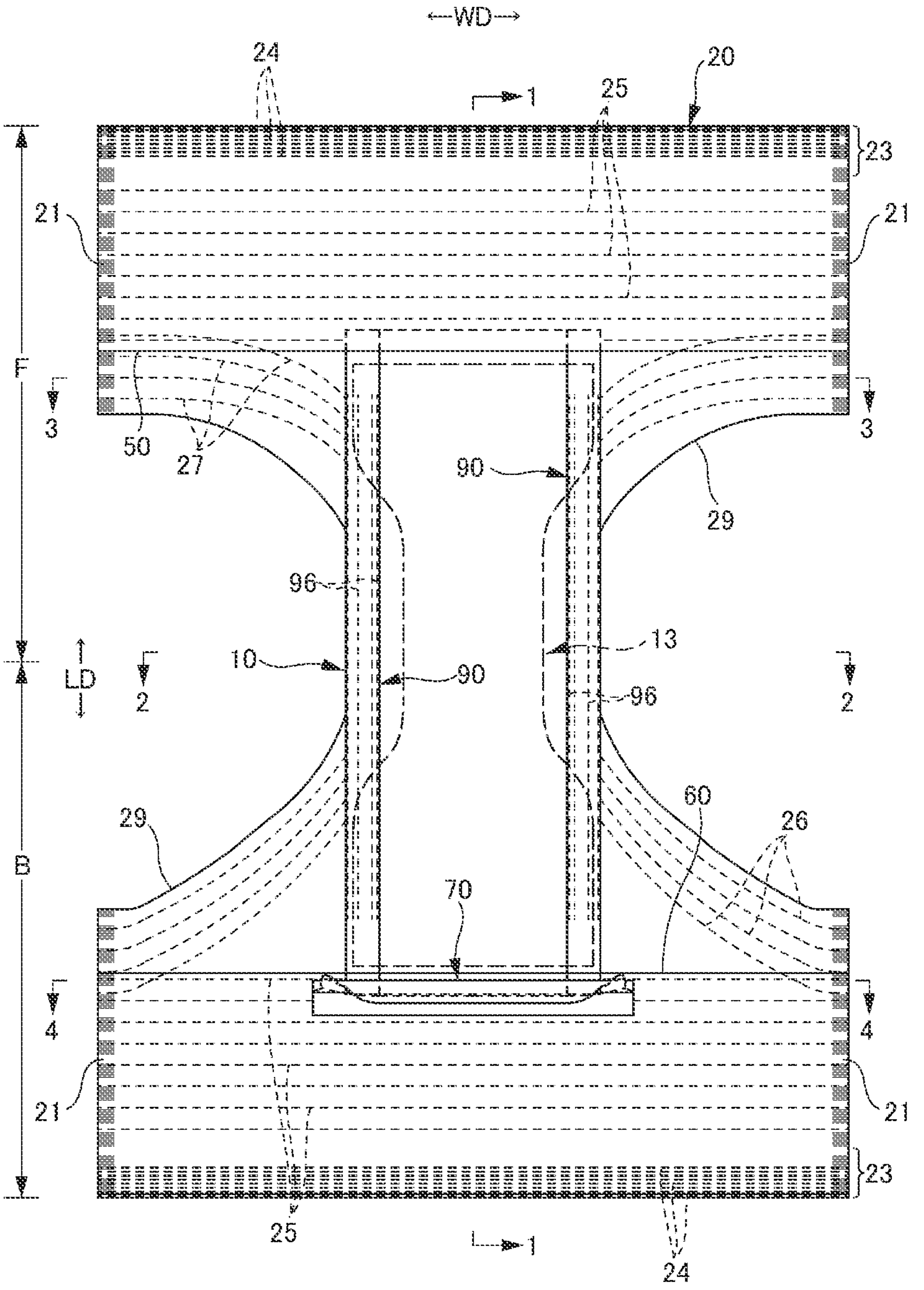

[FIG.2]
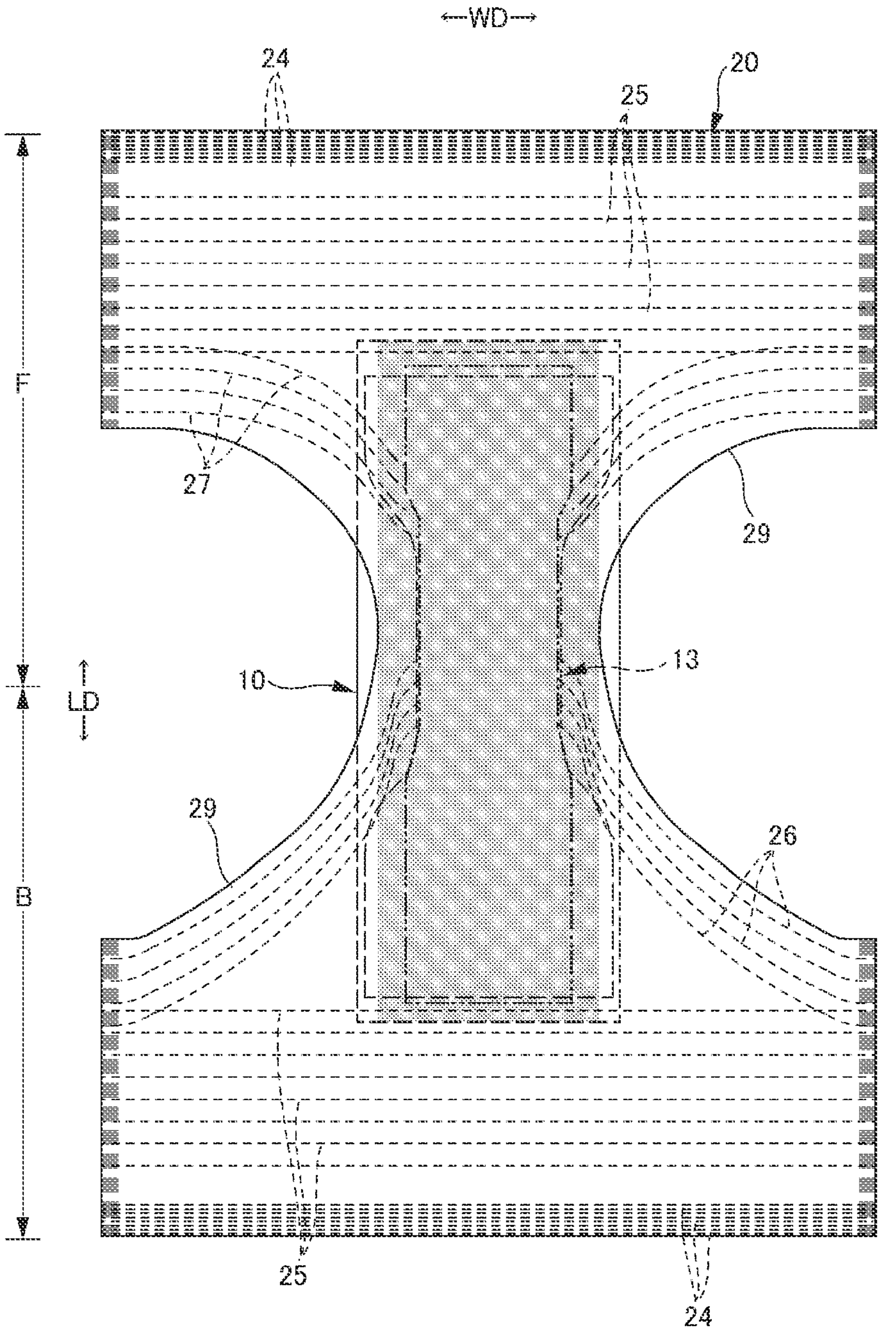

[FIG.3]
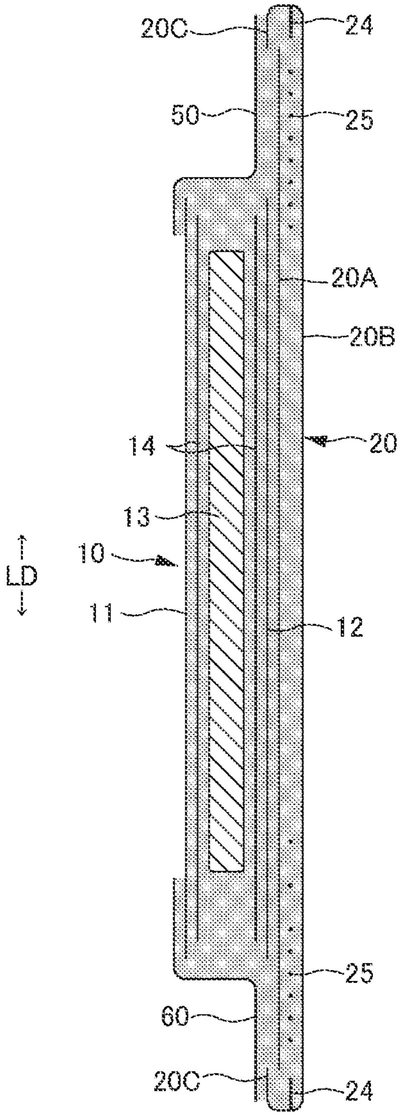

[FIG.4]
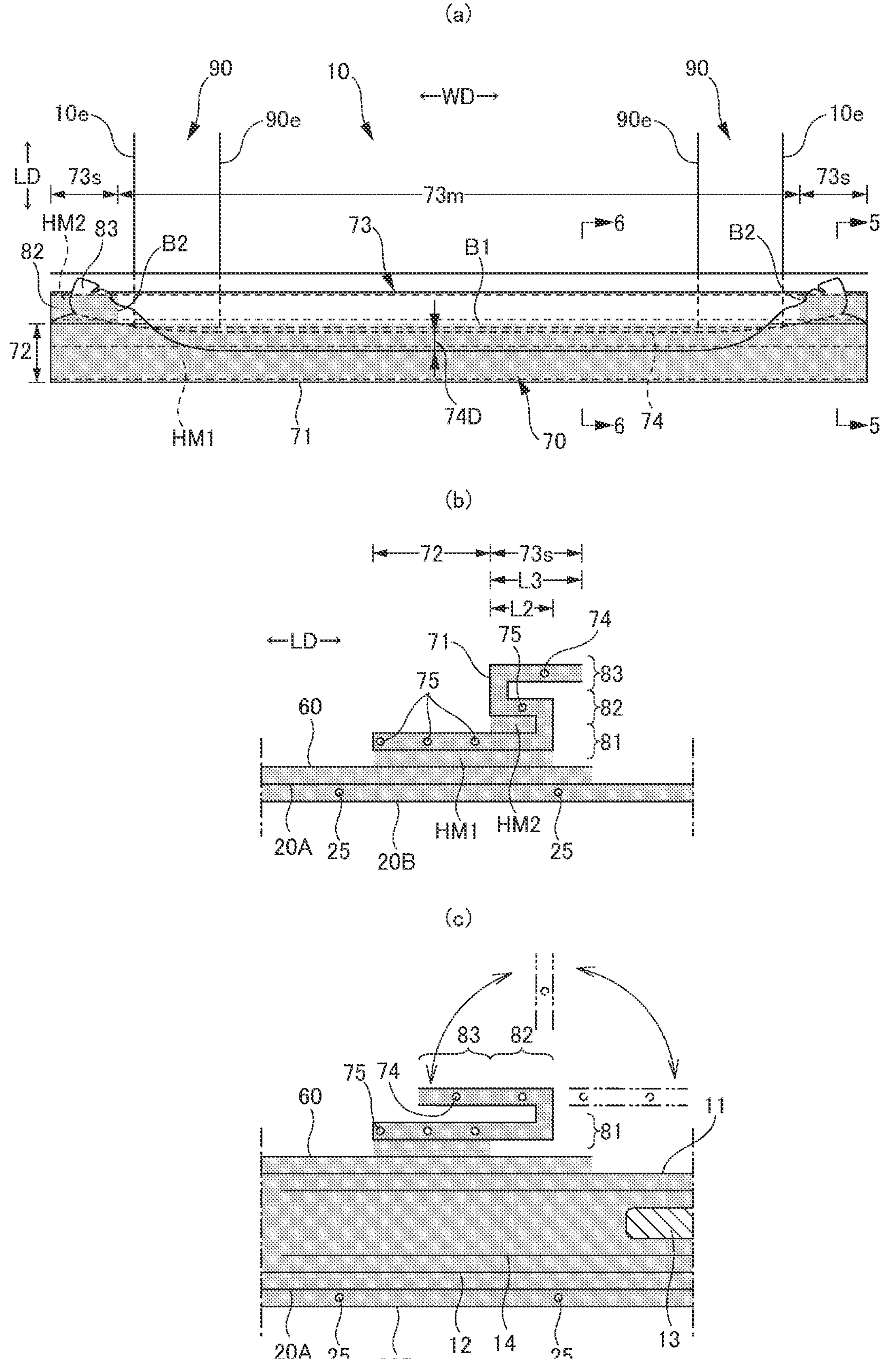

【FIG.5】
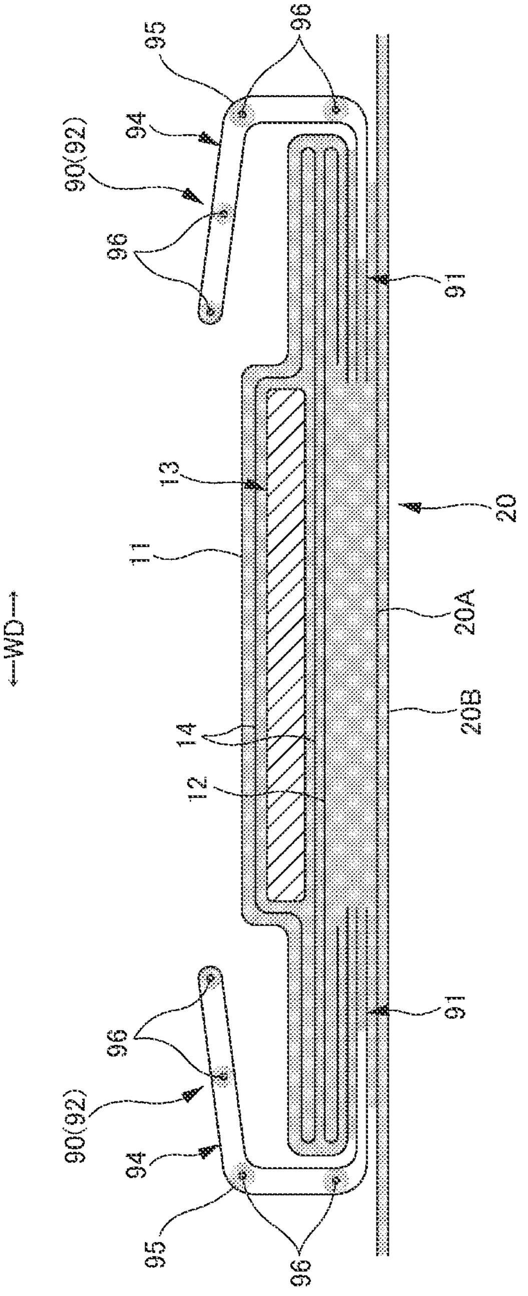

【FIG.6】
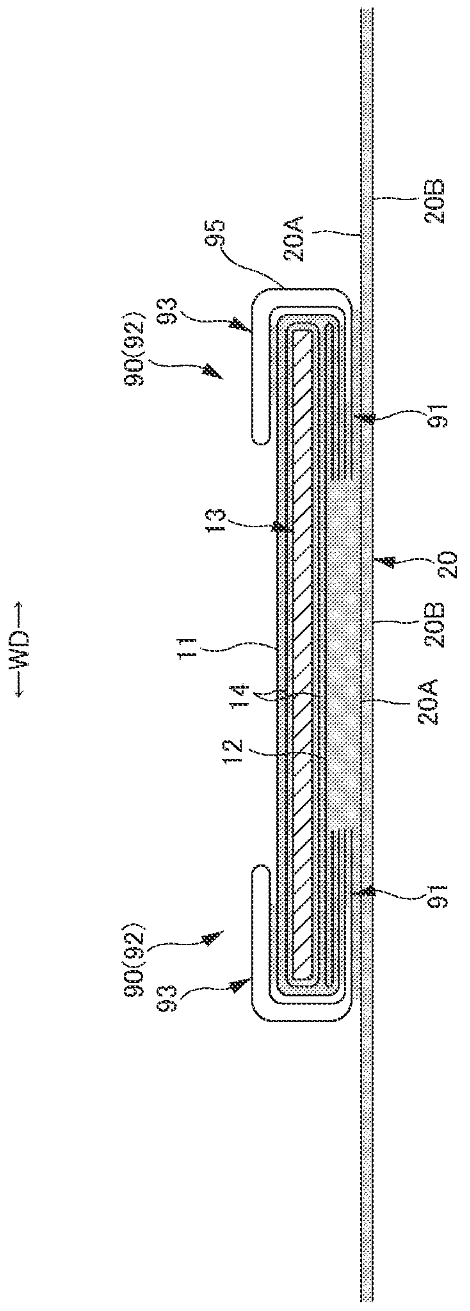

[FIG.7]
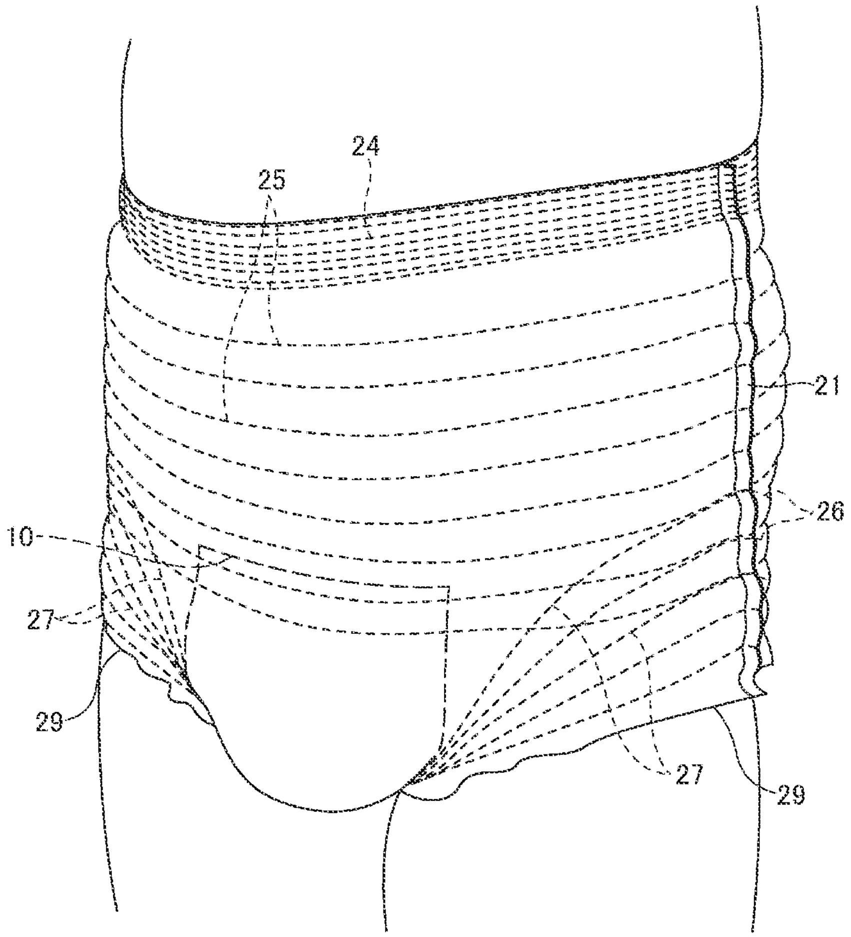

[FIG.8]
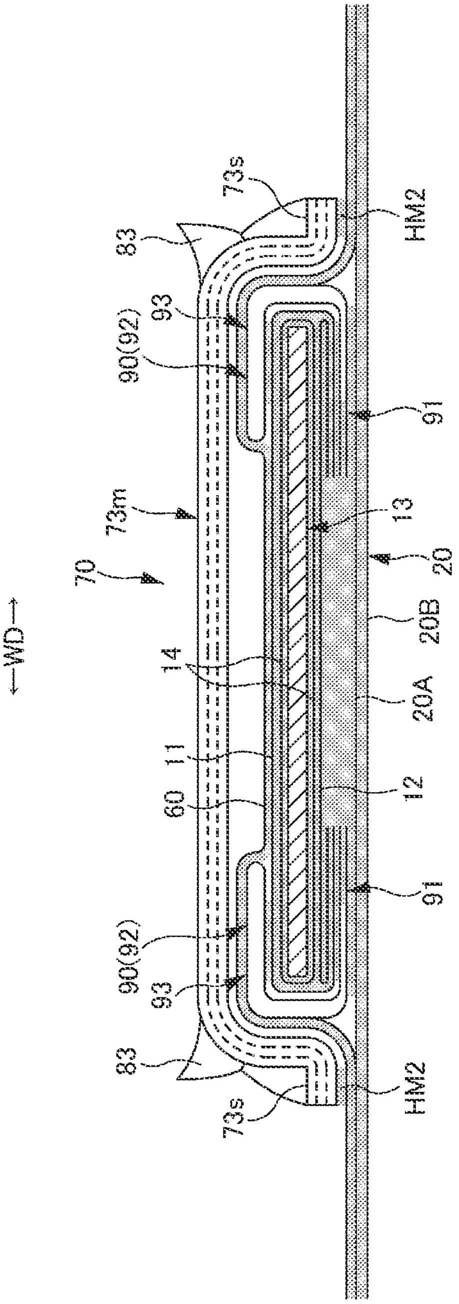

[FIG.9]
(a)
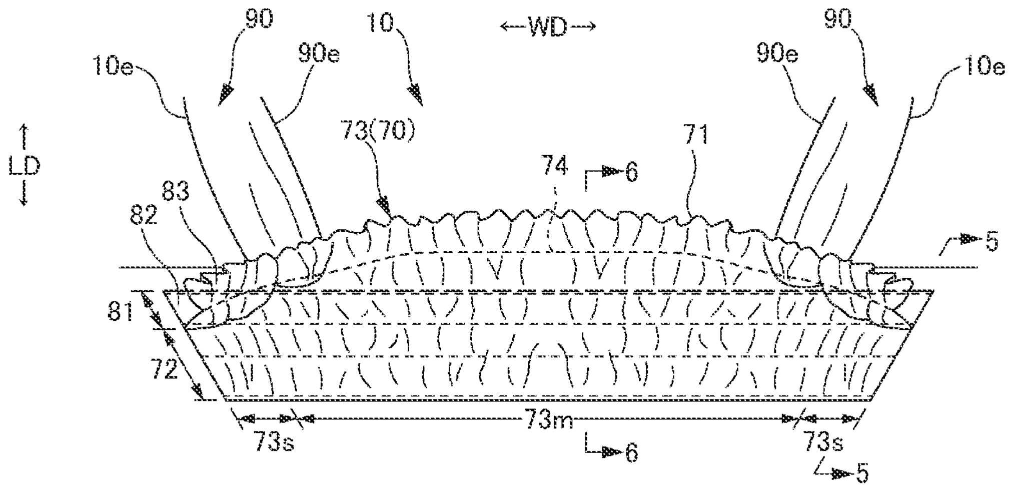
(b)
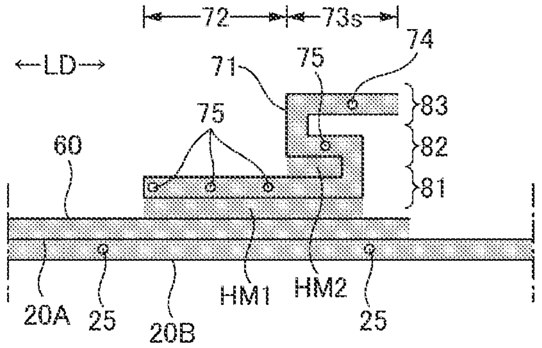
(c)
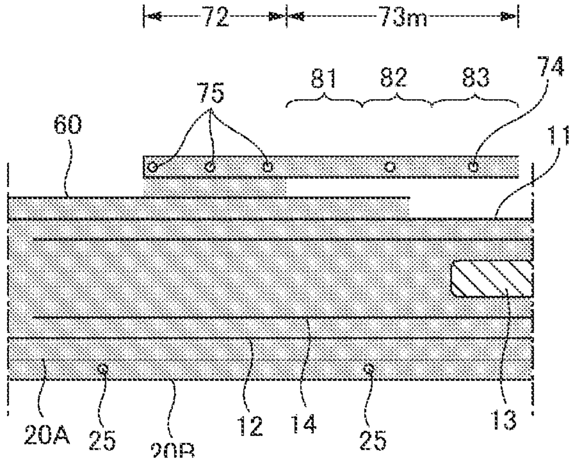

【FIG.10】
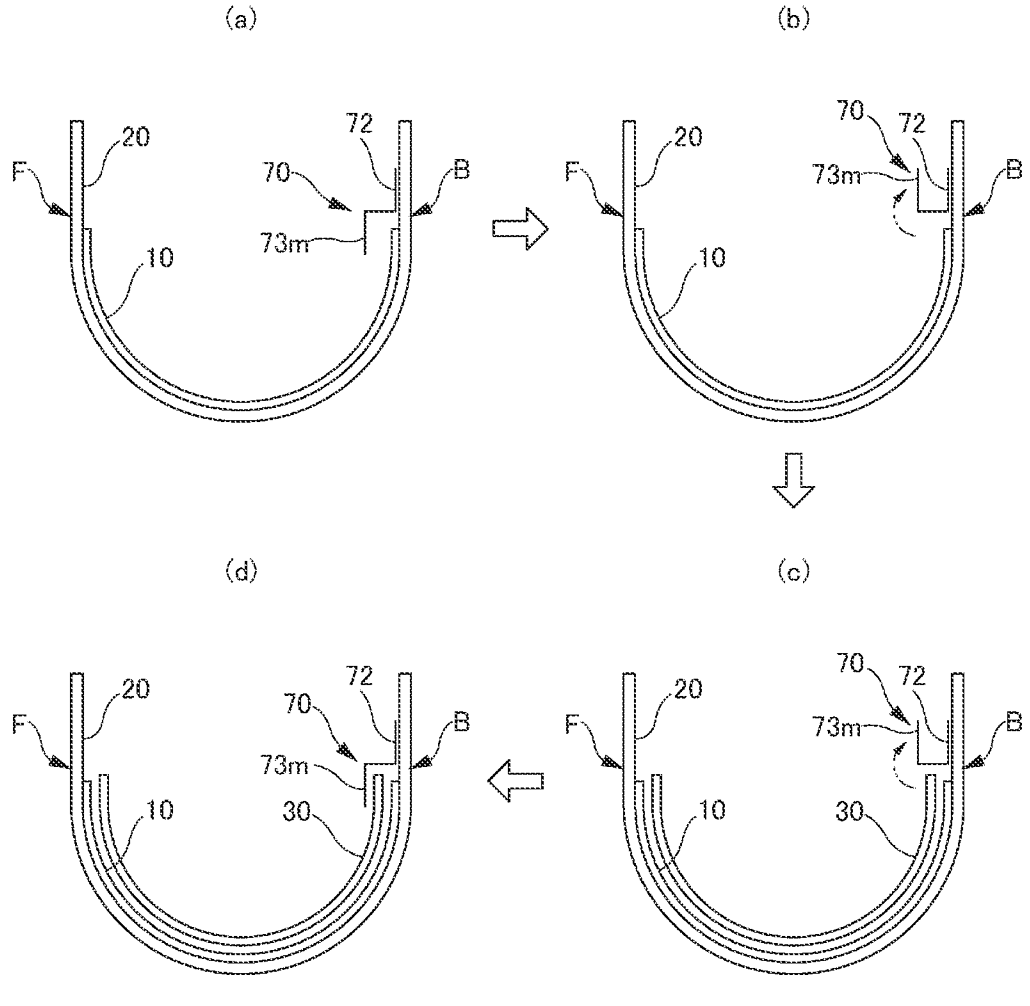

[FIG.11]
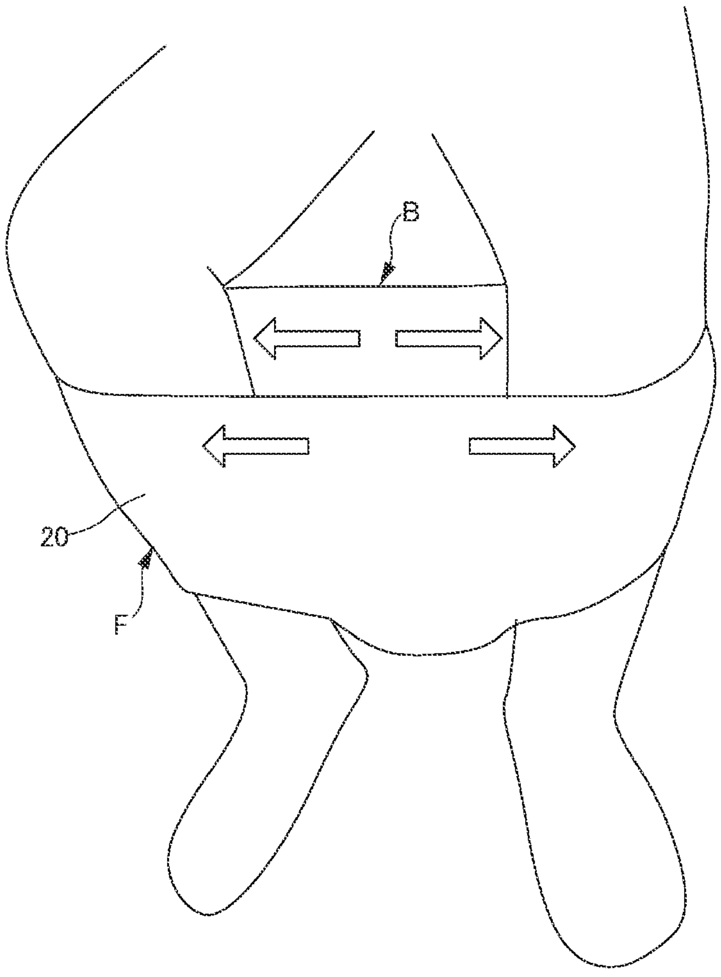

[FIG.12]
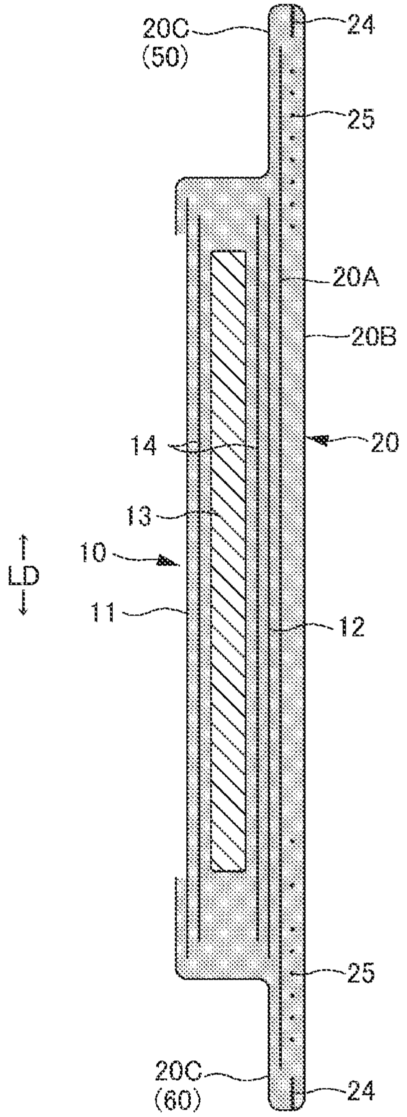

[FIG.13]
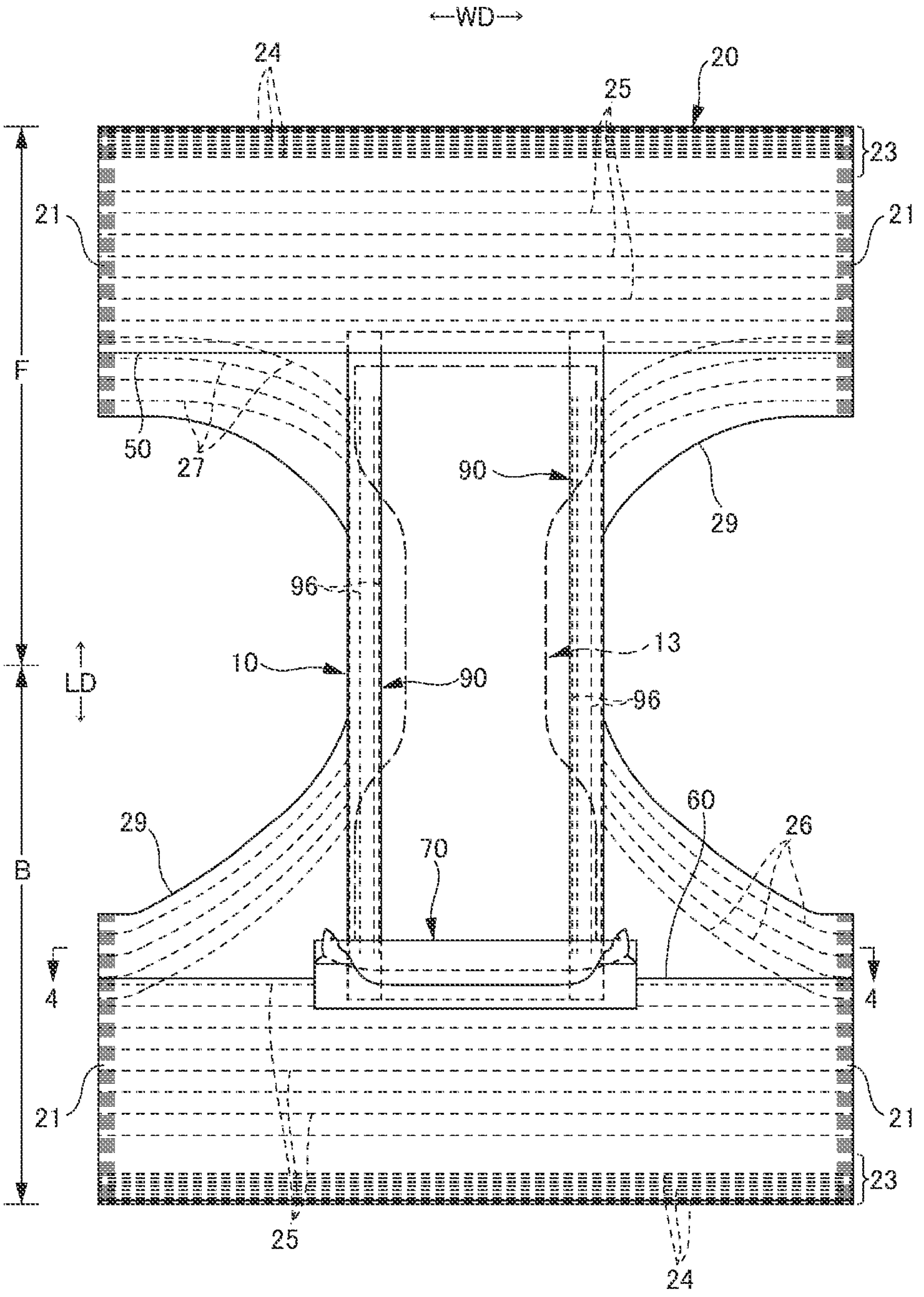

【FIG.14】
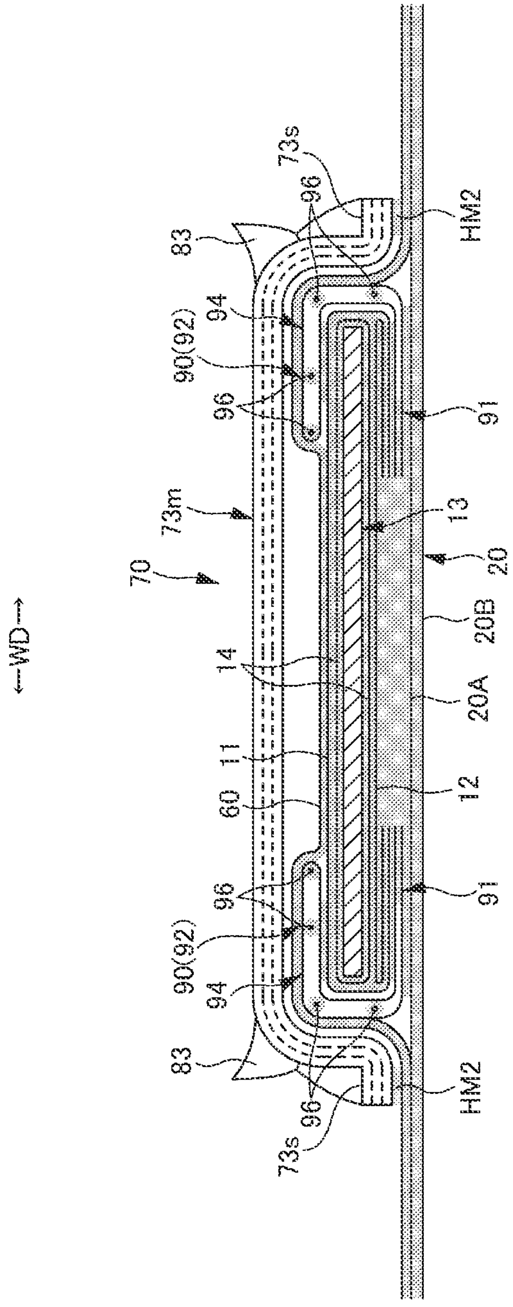

[FIG.15]
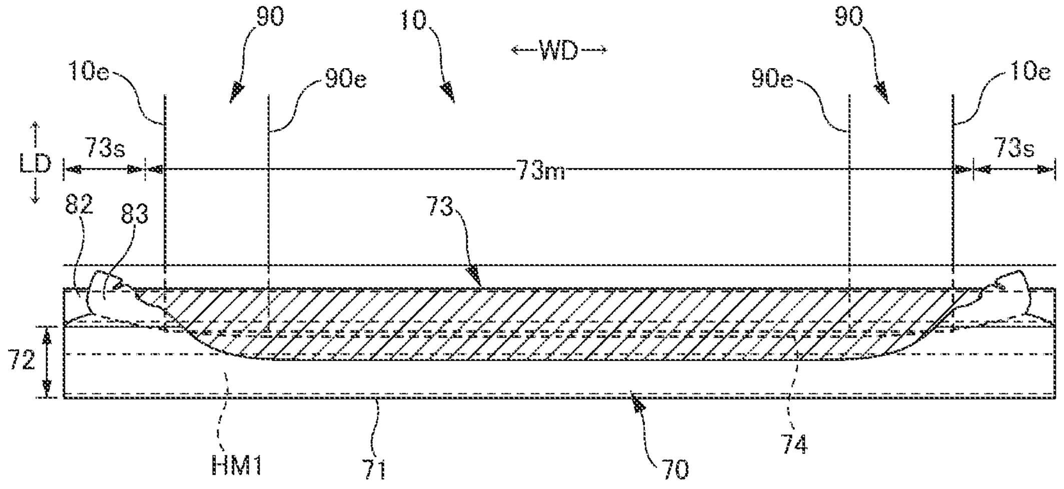

[FIG.16]
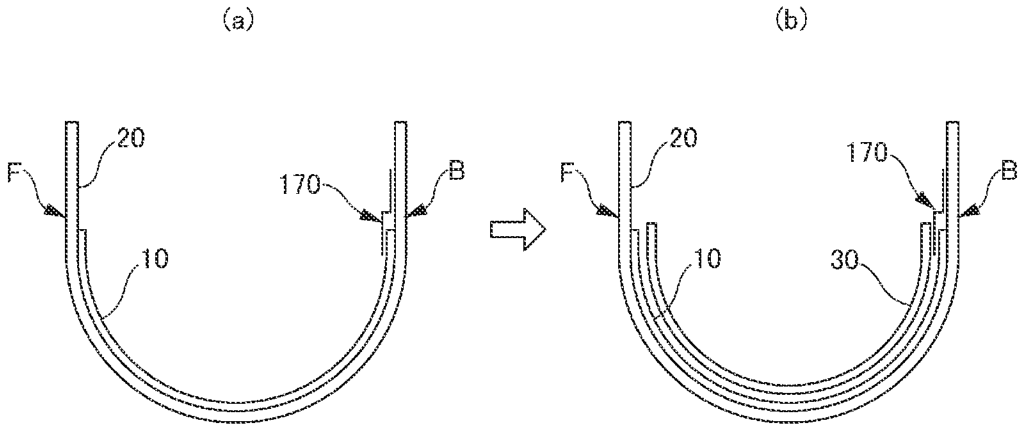

UNDERPANTS-TYPE DISPOSABLE WEARING ARTICLE

CROSS-REFERENCE TO RELATED APPLICATIONS

This application is the U.S. national stage application of International Application PCT/JP2022/001052, filed Jan. 14, 2022, which international application was published on Sep. 9, 2022, as International Publication WO 2022/185733 in the Japanese language. The International Application claims priority of Japanese Patent Application No. 2021-032655, filed Mar. 2, 2021. The international application and Japanese application are both incorporated herein by reference, in entirety.

TECHNICAL FIELD

The present invention relates to an underpants-type disposable wearing article having a function of preventing dorsal leakage.

BACKGROUND ART

An underpants-type disposable wearing article such as an underpants-type disposable diaper and an underpants-type sanitary article has elasticity along the width direction in a lower torso region thereof. Therefore, a gap is hardly formed between the wearer's back and the article. That is, excrement such as urine is hardly leaked from a dorsal side of the article (so-called dorsal leakage).

For example, a general underpants-type disposable diaper is provided with an outer member forming at least a lower torso portion of a front body part and a lower torso portion of a back body part, and an inner member including an absorber and being attached to the outer member so as to extend from the front body part to the back body part, and in the underpants-type disposable wearing article, both side edge portions of the outer member in the front body part and both side edge portions of the outer member in the back body part are bonded to each other, respectively so as to form side seal portions, thereby forming a waist opening and a pair of right and left leg opening portions. In the outer member, elastic members are provided in a lower torso region determined as a range in the front-back direction including the side seal portions (a range extending in the front-back direction from the waist opening to upper ends of the leg opening portions), thus, elasticity along the width direction is imparted to the lower torso region. As is known, not only an elongated elastic member such as a rubber thread but also an elastic film can be used as an elastic member (See, Patent Literatures 1 to 2, for example).

Due to such a high level of prevention of the dorsal leakage, there are users who are willing to use underpants-type disposable wearing articles while asleep for long time at night or the like. Additionally, in such a usage manner, it is still naturally more preferable that each of the underpants-type disposable wearing articles is provided with a dorsal side barrier. Therefore, it has been conventionally proposed that the dorsal side barrier is provided also in the underpants-type disposable wearing article (See, Patent Literature 1, for example).

However, there are cases when underpants-type disposable wearing articles provided with conventional dorsal side barriers are used while the dorsal side barriers thereof are flattened. Precisely, in producing such an underpants-type disposable wearing article, the dorsal side barrier is attached while a whole of it is flatly laid down. In addition, the dorsal side barrier is pressurized in a thickness direction in production. Not only that, even after production, the dorsal side barrier is pressurized in the thickness direction until a product of the underpants-type disposable wearing article is used. That is, even when the product is used, a standup section of the dorsal side barrier is remained to be attached weakly to a surface facing the standup section while the dorsal side barrier is laid down. Thus, if a user does not notice such a situation, the user would have to use the wearing article having an insufficient function of preventing leakage. It is therefore desired that the dorsal side barrier is made to stand up once when the underpants-type disposable wearing article is used.

Further, an underpants-type disposable wearing article may be used together with a pad-type absorbent article, which is to be laid on the internal surface of the article. In such case, if, by mistake, the pad-type absorbent article is laid on the dorsal side barrier, which is flatly laid down, there is a concern that the function of the dorsal side barrier is lost.

CITATION LIST

Patent Literature

Patent Literature 1: JP 2001-252303 A
Patent Literature 2: JP 2013-75106 A

SUMMARY OF INVENTION

Technical Problem

Therefore, a main object of the present invention is to provide an underpants-type disposable wearing article in which a dorsal side barrier can stand up unintentionally when the article is used.

Solution to Problem

An underpants-type disposable wearing article solving the above-mentioned problem is as follows.

<First Aspect>

An underpants-type disposable wearing article including an integrated outer member provided to extend from a front body part to a back body part or outer members separately provided for the front body part and the back body part, an inner member attached to a middle part of the outer member in a width direction and provided to extend from the front body part to the back body part, side seal portions in which both side portions of the outer member in the front body part and both side portions of the outer member in the back body part are bonded to each other, respectively, a waist opening and a pair of right and left leg opening portions, and a dorsal side barrier provided to be closer to the waist opening than a crotch portion in the back body part, wherein the dorsal side barrier includes a first blocking position for blocking a movement of excrement toward a back side, and second blocking positions for blocking movements of the excrement toward both sides in the width direction, the dorsal side barrier includes a barrier sheet having a width wider than that of the first blocking position and extending from a front side of the first blocking position to the back side thereof, the barrier sheet includes a base portion adjacent to the first blocking position on the back side thereof, and a main portion adjacent to the first blocking position on the front side thereof, the base portion is fixed to a top surface of the back body part, the main portion has both side portions adjacent to the second blocking positions on outer sides thereof and an intermediate portion disposed between the second blocking positions, each of both the side portions of the main portion has a first portion extending on the front side of the first blocking position, a second portion being folded back toward a top side at a folding position along a front edge of the first portion and extending backward, and a third portion being folded back toward the top side at a folding position along a back edge of the second portion and extending forward, an underside surface of the first portion is fixed to the top surface of the back body part, an underside surface of the second portion is fixed to a top surface of the first portion, and the third portion is unfixed to the second portion, the intermediate portion of the main portion is unfixed to the top surface of the back body part, an elongated barrier elastic member is provided to extend in the width direction from one of the third portions to the other of the third portions in the main portion, a back end portion of the third portion is free of the elongated barrier elastic member, and the main portion is elastically contracted in the width direction together with the elongated barrier elastic member in a natural length state.

(Effect)

The dorsal side barrier of the present underpants-type disposable wearing article has a characteristic folding back structure and a characteristic arrangement of the elongated barrier elastic member. Thus, in the natural length state, in the main portion of the barrier sheet, each of both the side portions has a folding back structure extending from the first portion to the second portion and a folding back structure extending from the second portion to the third portion, but the intermediate portion disposed between both the side portions is gradually unfolded to a front side with increasing proximity to a center side in the width direction so as to spread partway or completely to the front side at a center portion in the width direction (the first status).

The reason of this may not be clear, but it is possible to consider as follows: in the natural length state, the intermediate portion of the main portion is elastically contracted together with the barrier elastic member; here, the intermediate portion provided with the barrier elastic member is an unfixed free portion, and the barrier elastic member is provided only in a position separated from a back edge of the third portion, thus, the third portion is inclined freely to the center side in the width direction; incidentally, based on an elastic contraction force of the barrier elastic member, a force is applied to the intermediate portion of the main portion; a component of this force, in a direction along which the intermediate portion of the main portion is folded back in a similar way to both the side portions, becomes smaller due to the third portion inclined freely to the center side in the width direction; in this way, the first status is generated. Additionally, since contraction pleats extending in a front-back direction are formed all over the intermediate portion of the main portion, a stiffness of the main portion becomes higher (which makes it difficult for the main portion to be folded and to be bent in the front-back direction). It is considered that this high stiffness also affects the intermediate portion of the main portion to be unfolded so as to spread.

On the other hand, for wearing the article, as the main portion of the barrier sheet is made to be stretched in the width direction together with the barrier elastic member, in each of both the side portions of the main portion, the folding back structure continued from the first portion to the second portion is maintained and the folding back structure continued from the second portion to the third portion is maintained to a certain extent. However, in the intermediate portion of the main portion, a portion (hereinafter, also referred to as a pivot portion), which is located to be closer to a front end edge of the main portion than an imaginary line extending in the width direction so as to pass along a boundary (folding back position) between the first portion and the second portion, pivots backward around the imaginary line (the second status).

The reason of this may not be clear either, but it is possible to consider as follows: for wearing the article, the barrier elastic member is stretched so as to be closely analogous to a straight line along the width direction; based on the elastic contraction force of the barrier elastic member, the force is applied to the intermediate portion of the main portion; the component of this force, in the direction along which the intermediate portion of the main portion is folded back in the similar way to both the side portions, becomes larger due to the barrier elastic member stretched so as to be closely analogous to the straight line along the width direction; on the other hand, a folding force hardly applies to the third portion since the third portion is unfixed all over the width direction; in this way, the second status is generated. Incidentally, the degree of the pivoting can be adjusted properly by the arrangement of the barrier elastic member and the like. Depending on the degree of pivoting, the third portion can pivot so as to stand up slightly from the natural length state, the third portion can pivot so as to fall over backward (toward a waist opening) which is opposite to the natural length state, or the like.

As is known from the change in the first status and in the second status discussed above, in a worn state where the intermediate portion of the main portion is contracted to a certain degree, a pocket open to a crotch portion is formed between the intermediate portion of the main portion and the top surface of the back body part, because the intermediate portion of the main portion is unfixed to the top surface of the back body part, while the base portion located at the back side of the intermediate portion and both the side portions located on both the sides of the intermediate portion in the main portion are fixed to the top surface of the back body part directly or indirectly. As a result, when excrement reaches the pocket, the movement of the excrement toward the back side and the movements of the excrement toward both the sides can be prevented by the pocket.

As stated above, in the present underpants-type disposable wearing article, the dorsal side barrier changes as in the above mentioned first status, as in the second status, and as in the worn state. Thus, when the article is used, the dorsal side barrier can stand up automatically, so that a case where the article is used while the dorsal side barrier is flattened and a case where by mistake, the pad-type absorbent article is laid on the dorsal side barrier, which is flatly laid down, is less likely to occur.

<Second Aspect>

The underpants-type disposable wearing article according to the first aspect, wherein the intermediate portion of the main portion has a dimension in the width direction of 180 to 200 mm, the second portion has a dimension in a front-back direction of 5 to 25 mm, the third portion has a dimension in the front-back direction of 10 to 35 mm, the third portion has a stretch rate in the width direction at a maximum stretch of 180 to 280%, and an interval in the front-back direction between a back edge of the third portion and the elongated barrier elastic member is 3 to 20 mm.

(Effect)

The dimensions of each portion of the elongated barrier sheet may be determined appropriately. However, these dimensions are preferably within the ranges of the present aspect, because under a situation where the third portion is stretched at a stretch rate being 0.4 times or more the stretch rate at the maximum stretch, the above mentioned pivot portion may pivot about 90 degrees or more with respect to the top surface of the back body part, then, reaching a situation where the third portion is stretched at a stretch rate being 0.6 times or more the stretch rate at the maximum stretch, the pivot portion may fall down on the back side (the waist opening side).

<Third Aspect>

The underpants-type disposable wearing article according to the first or second aspect, further including at least one elongated shaping elastic member selected from an elongated shaping elastic member provided to extend in the width direction from one of the second portions to the other of the second portions in the main portion, an elongated shaping elastic member provided to extend in the width direction from one of the first portions to the other of the first portions in the main portion, and an elongated shaping elastic member provided to extend in the width direction across both side portions of the base portion, wherein the main portion is elastically contracted in the width direction together with the selected at least one elongated shaping elastic member in the natural length state.

(Effect)

As in the present aspect, in addition to the elongated barrier elastic member, which is provided to extend through the third portions, the elongated shaping elastic member, which is provided to extend through at least one of the first portion, the second portion and the base portion, is preferably provided, because a shape of the dorsal side barrier may be arranged and in addition to this, it becomes easier for the intermediate portion of the main portion to be unfolded so as to spread in the natural length state.

<Fourth Aspect>

The underpants-type disposable wearing article according to any one of the first to third aspects, wherein the inner member has an absorber provided in a range including the crotch portion, the outer member has, in a front-back direction range including the side seal portions, a lower torso stretchable region, which is elastically contracted in the width direction, and a non-stretchable region, which is located in a middle part in the width direction of a range overlapping with the absorber, the lower torso stretchable region has a portion, which is adjacent to the absorber at a back end on the waist opening side thereof, and the base portion of the barrier sheet is fixed to the portion, which is adjacent to the absorber at the back end on the waist opening side thereof, to be stretchable together with the lower torso stretchable region.

(Effect)

In many cases, an underpants-type disposable wearing article including the absorber has a lower torso stretchable region as in the present aspect. Due to the lower torso stretchable region, it is possible to press the back end of the absorber and a vicinity thereof firmly against skin of a wearer. Further, it is general that a portion overlapping with the absorber in the outer member is free of the stretchable region. The present aspect is characterized in that such a lower torso stretchable region is utilized. Precisely, it is preferable that the base portion of the barrier sheet is fixed to the portion, which is adjacent to the absorber at the back end on the waist opening side thereof in the lower torso stretchable region, to be stretchable together with the lower torso stretchable region, because the shape of the dorsal side barrier may be arranged, and in addition to this, it may become easier for the intermediate portion of the main portion to be unfolded so as to spread in the natural length state.

<Fifth Aspect>

The disposable wearing article according to any one of the first to fourth aspects, wherein at least in the intermediate portion of the main portion in the barrier sheet, a color, a pattern or a representation of a top surface thereof is different from a color, a pattern or a representation of an underside surface thereof, respectively.

(Effect)

In a case of the present aspect, a user can easily recognize automatic deformation of the above mentioned dorsal side barrier (change from the first status to the second status). Therefore, for example, when the present underpants-type disposable wearing article is used together with a pad-type absorbent article, which is to be laid on the internal surface of the article, it becomes easier for the user to recognize an appropriate position for laying the pad-type absorbent article thereon.

Advantageous Effects of Invention

As will be appreciated from the foregoing, the present invention provides advantages such as an ability of a dorsal side barrier to stand up unintentionally when the present underpants-type disposable article is used.

BRIEF DESCRIPTION OF DRAWINGS

FIG. 1 is a plan view (internal surface side) of an underpants-type disposable diaper in a spread state.

FIG. 2 is a plan view (external surface side) of the underpants-type disposable diaper in the spread state.

FIG. 3 is a cross-sectional view taken along 1-1 line of FIG. 1 for showing the underpants-type disposable diaper exclusive of a dorsal side barrier.

FIG. 4(*a*) is a plan view of the dorsal side barrier in the spread state, FIG. 4(*b*) is a cross-sectional view taken along 5-5 line of FIG. 4(*a*), and FIG. 4(*c*) is a cross-sectional view taken along 6-6 line of FIG. 4(*a*).

FIG. 5 is a cross-sectional view taken along 2-2 line of FIG. 1.

FIG. 6 is a cross-sectional view taken along 3-3 line of FIG. 1.

FIG. 7 is a perspective view of the underpants-type disposable diaper in a worn state.

FIG. 8 is a cross-sectional view taken along 4-4 line of FIG. 1.

FIG. 9(*a*) is a plan view showing the dorsal side barrier in a natural length state, FIG. 9(*b*) is a cross-sectional view taken along 5-5 line of FIG. 9(*a*), FIG. 9(*c*) is a cross-sectional view taken along 6-6 line of FIG. 9(*a*).

FIG. 10 is a cross-sectional view showing change of a main part in a process of wearing the diaper.

FIG. 11 is a perspective view showing the underpants-type disposable diaper in the stretched state when the diaper is being worn.

FIG. 12 is a cross-sectional view showing another underpants-type disposable diaper exclusive of a dorsal side barrier.

FIG. 13 is a plan view (internal surface side) of the underpants-type disposable diaper in the spread state.

FIG. 14 is a cross-sectional view taken along 4-4 line of FIG. 13.

FIG. 15 is a plan view showing the dorsal side barrier in the spread state.

FIG. 16 is a cross-sectional view showing change of a main part in a process of wearing a conventional diaper.

DESCRIPTION OF EMBODIMENTS

Hereinafter, a detailed description will be given of an example of an underpants-type disposable diaper, referring to accompanying drawings. Incidentally, each of dotted pattern regions in the drawings indicates an adhesive as bonding means that bonds respective components located on the top side and an underside thereof, and is formed by solid, bead, curtain, summit, or spiral coating of a hot melt adhesive, or pattern coating (transfer of the hot melt adhesive in a letterpress method), or application of the hot melt adhesive to an outer peripheral surface of an elastic member such as comb gun or sure wrap application instead of or together with the above methods in a fixed part of the elastic member. Examples of the hot melt adhesive include EVA-based, pressure sensitive adhesion rubber-based (elastomer-based), polyolefin-based, and polyester/polyamide-based adhesives, and can be used without any particular limitation. As bonding means that bonds respective components, it is possible to use means by material welding such as heat sealing or ultrasonic sealing.

FIG. 1 to FIG. 7 show an underpants-type disposable diaper. The underpants-type disposable diaper (hereinafter also simply referred to as a diaper) includes an integrated outer member 20 provided to extend from a front body part F to a back body part B, and an inner member 10 provided to extend from the front body part F to the back body part B to attach to an internal surface of the outer member 20, and the inner member 10 is formed by interposing an absorber 13 between a liquid pervious top sheet 11 and a liquid impervious sheet 12. In manufacturing, after an underside surface of the inner member 10 is bonded to the internal surface (upper surface) of the outer member 20 by bonding means such as a hotmelt adhesive (the dotted pattern region in FIG. 2), the inner member 10 and the outer member 20 are folded at a center in a front-back direction LD (longitudinal direction) corresponding to a boundary between the front body part F and the back body part B, and both side portions thereof are bonded to each other by thermal welding or the hotmelt adhesive to form side seal portions 21, thereby obtaining the underpants-type disposable diaper in which a waist opening and a pair of right and left leg opening portions are formed. Outer members 20 may be separately provided for the front body part F and the back body part B.

(Structure Example of Inner Member)

As illustrated in FIG. 4 to FIG. 6, the inner member 10 has a structure in which the absorber 13 is interposed between the liquid pervious top sheet 11 and the liquid impervious sheet 12 and absorbs and holds excretion fluid passing through the top sheet 11 by means of the absorber 13. A planar shape of the inner member 10 is not particularly limited. However, a substantially rectangular shape is generally adopted as the illustrated embodiment.

As the top sheet 11 that covers the top side (skin contact surface side) of the absorber 13, a perforated or non-perforated nonwoven fabric, a porous plastic sheet, etc. is preferably used. As a material fiber constituting the nonwoven fabric, it is possible to adopt a regenerated fiber such as rayon and cupra or a natural fiber such as cotton in addition to a polyolefin-based synthetic fiber such as polyethylene or polypropylene, a polyester-based synthetic fiber, a polyamide-based synthetic fiber, etc., and it is possible to use a nonwoven fabric obtained by an appropriate processing method such as a spunlace method, a spunbond method, a thermal bond method, a meltblown method, a needle punch method, etc. In these processing methods, the spun lace method is excellent in terms of flexibility and drapability, and the thermal bond method is excellent in terms of bulkiness and softness. When a large number of through holes are formed on the top sheet 11, urine and the like are quickly absorbed. In the illustrated embodiment, the top sheet 11 is wound around side edge portions of the absorber 13 and extends to an underside of the absorber 13.

As the liquid impervious sheet 12 covering the underside (non-skin contact surface side) of the absorber 13, a liquid impervious plastic sheet such as polyethylene or polypropylene may be used. However, in recent years, a sheet having a moisture penetration property may be preferably used from a viewpoint of preventing stuffiness. As this liquid impervious and moisture permeable sheet, for example, a microporous sheet may be favorably used which is obtained by melt-kneading an inorganic filler such as calcium carbonate in a polyolefin resin such as polyethylene or polypropylene, molding the melt-kneaded mixture into a sheet, and then stretching the sheet in one or two axial directions. In the illustrated embodiment, the liquid impervious sheet 12 is folded back to the underside together with the top sheet 11 at both sides of the absorber 13 in the width direction WD, but is not limited thereto and other known structures may be employed.

As the absorber 13, it is possible to use a known one, which is based on, for example, a pulp fiber stack, an assembly of filaments of cellulose acetate, etc., or a nonwoven fabric and which has superabsorbent polymer mixed therewith or fixed thereto, or the like as necessary. The entire shape of the absorber 13 is formed into a substantially hourglass shape having a narrower portion narrower than both front and back sides at a crotch portion. Alternatively, it may have an appropriate shape such as a rectangular shape. As long as the absorber 13 is provided in a range including a crotch portion of the inner member 10, the absorber 13 may be provided only in a part of the inner member 10. However, in a normal case, the absorber 13 is desirably provided all over a region of the inner member 10 exclusive of the front and back end portions thereof.

To hold the shape and the polymer particles and for other purposes, the absorber 13 can be wrapped in a wrapping sheet 14 having a liquid pervious and liquid retaining property such as crepe paper as necessary. The wrapping sheet 14 may be tissue paper, in particular, crepe paper, nonwoven fabric, polyethylene-laminated nonwoven fabric, perforated sheet, or the like, provided that sheets through which the super absorbent polymer particles will not escape are preferred. When nonwoven fabric is used in place of crepe paper, hydrophilic SMS (SMS, SSMMS, or the like) nonwoven fabric is particularly preferred, which may be made of polypropylene, polyethylene/polypropylene composite material, or the like. The basis weight of the wrapping sheet 14 is preferably 5 to 40 g/m$^2$, particularly 10 to 30 g/m$^2$.

A wrapping mode with the wrapping sheet 14 may be determined appropriately. However, in view of ease of manufacturing and in view of limiting escape of the super absorbent polymer particles from front and back end edges of the wrapping sheet 14, the following mode is preferable. Precisely, the wrapping sheet 14 winds around the absorber 13 in a tubular shape so as to surround a top surface, an underside surface, and both side surfaces thereof, while a front end edge portion and a back end edge portion of the wrapping sheet 14 are made to protrude forward and backward from the absorber 13, respectively. Overwrapped portions of the wrapping sheet 14 wound around the absorber 13 and overwrapped portions of the wrapping sheet 14 protruded from the absorber 13, respectively, are bonded to each other, by bonding means such as a hot melt adhesive or material welding.

Standup gather parts 90 are provided on both sides of the inner member 10 in the width direction WD. Each of the standup gather parts 90 includes a standup portion 94 standing up from a side portion of the inner member 10. This standup portion 94 is brought into contact with a range from an inguinal region to a gluteal region through a round-leg portion of a wearer for preventing side leakage. In more detail, as shown in FIG. 5 and FIG. 6, each of the standup gather parts 90 in the illustrated example includes a gather fixed portion 91 fixed to a side portion of an underside surface of the inner member 10, a main unit section 92 extending from the gather fixed portion 91 up to a side portion of a top surface of the inner member 10 through a lateral side of the inner member 10, a fallen portion 93 formed by front and back end portions of the main unit section 92 fixed to the side portion of the top surface of the inner member 10 in a fallen state, and the standup portion 94 formed between parts of the fallen portion 93 to be unfixed. Each of these portions has a two-layered structure formed by folding a gather sheet 95. Further, between these two layers, elongated gather elastic members 96 are disposed at a front end edge portion and the like of the standup portion 94. According to this configuration, the standup portion 94 of the standup gather part 90 is made to stand up so as to be brought into contact with the skin of the wearer. As the gather sheet a nonwoven fabric which is rendered water repellent may be used favorably.

As the gather elastic member 96, it is possible to use a normally used material such as polystyrene-based rubber, polyolefin-based rubber, polyurethane-based rubber, polyester-based rubber, polyurethane, polyethylene, polystyrene, styrene-butadiene copolymer, silicone, polyester, etc. In addition, to make it difficult to see from the outside, it is preferable that a fineness is set to 925 dtex or less, a tension is set to 150 to 350%, and an interval is set to 7.0 mm or less. Incidentally, as the gather elastic member 96, it is possible to use a tape-like member having a certain width in addition to a thread-like member as in the illustrated embodiment.

As a material fiber constituting the gather sheet described above, similarly to the top sheet 11, it is possible to adopt a regenerated fiber such as rayon or cupra or a natural fiber such as cotton in addition to a polyolefin-based synthetic fiber such as polyethylene or polypropylene, a polyester-based synthetic fiber, a polyamide-based synthetic fiber, etc., and it is possible to use a nonwoven fabric obtained by an appropriate processing method such as a spunbond method, a thermal bond method, a meltblown method, a needle punch method, etc. However, in particular, in order to prevent stuffiness, it is preferable to use a nonwoven fabric that suppresses a basis weight and has excellent air permeability. Further, with regard to the gather sheet 95, to prevent passage of urine, etc., prevent a rash, and enhance a feel to a skin (dry feeling), it is preferable to use a water repellent nonwoven fabric coated with a silicone-based, paraffin metal-based, or alkylchromic chloride-based water repellent agent, etc.

(Structure Example of Outer Member)

As shown also in FIG. 4 to FIG. 6, the outer member 20 has a two-layered structure including a pressing sheet 20A and a back sheet 20B each of which is made of a nonwoven fabric or the like, and the elasticity is imparted to the outer member 20 by disposing elastic members 24 to 27 between the pressing sheet 20A and the back sheet 20B and between the nonwoven fabrics of a folded portion 20C formed by folding the back sheet 20B toward the internal surface side at a waist opening edge such that the outer member 20 is contracted by contraction forces of the elastic members 24 to 27 in a natural length state. A planar shape of the outer member 20 is substantially hourglass shaped as a whole, by concave around-leg lines 29 configured so as to form leg opening portions on both side portions of a middle part of the outer member 20 in the front-back direction LD.

In the outer member 20 of the illustrated embodiment, as the elastic members, in a spread shape shown in FIG. 1 and FIG. 2, a waist elastic member 24 is arranged in a vicinity 23 of the waist opening, and in each of the front body part F and the back body part B, a plurality of under-waist elastic members 25 is arranged along the width direction WD at intervals in the longitudinal direction, and besides the under-waist elastic members 25, a plurality of curved elastic members 26, 27 is arranged at intervals without crossing each other in a curved pattern of extending from one of the side seal portions 21 along one of the leg opening portions toward the crotch portion, crossing the crotch portion, and extending along the other of the leg opening portions to reach the other of the side seal portions 21. Each of the elastic members 24 to 27 is fixed in a state of being stretched at a predetermined stretch rate along the extending direction thereof. Incidentally, in the present outer member 20, so-called around-leg elastic members, which are arranged continuously from the side seal portions of the front body part F to the side seal portions of the back body part B along the around-leg lines 29, are not provided.

The waist elastic member 24 is an elongated elastic member such as a plurality of rubber threads arranged at intervals in the longitudinal direction at a vicinity of a waist opening edge in a longitudinal direction range of the side seal portions 21 where the front body part F and the back body part B are bonded, and the waist elastic member 24 applies a stretching force to tighten a waist circumference of the wearer's body such that the diaper is put on the body. For the waist elastic member 24 in the illustrated example, thread rubbers are used, but for example, a tape-like elastic member may be used. Further, the waist elastic member 24 in the illustrated embodiment is sandwiched between the nonwoven fabrics of the folded portion 20C of the back sheet 20B in the waist portion, but it may be sandwiched between the pressing sheet 20A and the back sheet 20B.

The under-waist elastic members 25 are elongated elastic members such as rubber threads arranged at intervals in the longitudinal direction substantially in a range from an upper portion to a lower portion within the side seal portions 21, and the under-waist elastic members 25 apply stretching forces in the width direction WD to a lower torso portion of each of the front body part F and the back body part B such that the diaper is fit to the wearer's body. Incidentally, a boundary between the waist elastic member 24 and the under-waist elastic members 25 may not be necessarily clear. For example, among elastic members arranged along the width direction WD at intervals in the longitudinal direction in each of the front body part F and the back body part B, several number, although the number cannot be specified, of elastic members arranged in an upper portion side function as the waist elastic member, whilst remained elastic members function as the under-waist elastic members.

In the back body part B, a dorsal side curved elastic member 26 provided so as to separate from the under-waist elastic members 25 is an elongated elastic member such as a rubber thread, and is disposed along a predetermined curve. Although one dorsal side curved elastic member 26 may be provided, it is preferable that a plurality of dorsal side curved elastic members 26 is provided. In the illustrated example, four dorsal side curved elastic members 26 such as rubber threads are provided at each side of the outer member 20. These dorsal side curved elastic members 26 do not cross each other but are disposed at intervals therebetween. As for the arrangement of the dorsal side curved elastic members 26, instead of a group of about two or three elastic members arranged as a substantially bundle with being closely spaced, three or more, preferably four or more elastic members are arranged at intervals of about 3 to 20 mm, preferably about 6 to 16 mm so as to form a predetermined stretchable zone.

In the front body part F of the outer member 20, a ventral side curved elastic member 27 provided so as to separate from the under-waist elastic members 25 is an elongated elastic member such as a rubber thread, and is disposed along a predetermined curve. Although one ventral side curved elastic member 27 may be provided, it is preferable that a plurality of ventral side curved elastic members 27 is provided. In the illustrated example, four ventral side curved elastic members 27 such as rubber threads are provided at each side of the outer member 20. These ventral side curved elastic members 27 do not cross each other but are disposed at intervals therebetween. Also as for the arrangement of the ventral side curved elastic members 27, instead of a group of about two or three elastic members arranged as a substantially bundle with being closely spaced, more than three, preferably more than four elastic members are arranged at intervals of about 3 to 20 mm, preferably about 6 to 16 mm so as to form a predetermined stretchable zone.

Incidentally, as shown in FIG. 2, the under-waist elastic members 25 and the curved elastic members 26, 27 arranged in each of the front body part F and in the back body part B are continuously fixed to the outer member 20 at the time of manufacturing, and then, parts of the elastic members in a middle area in the width direction WD overlapping with the absorber 13 (an area surrounded by an alternate long and two short dashes line) may be finely cut according to a predetermined cutting pattern to form a non-contractible area to which contraction force is not applied. An area extending laterally from the non-contractible area may become a contractible area (that is, the area in which the under-waist elastic members 25 and the curved elastic members 26, 27 are continuously remained) to which contraction force is applied. Thereby, it is possible to prevent unnecessary contraction in the width direction WD of the inner member (in particular, the absorber 13). Naturally, the under-waist elastic members and the curved elastic members 26, 27 may be arranged continuously across the inner member 10.

As is known from this example, among areas where the elastic members 24 to 27 are arranged, the contractible area becomes a stretchable region, while the non-contractible area becomes a non-stretchable region. The stretchable region may be provided at only a portion located to be closer to the waist opening than the back end portion of the absorber 13 in the back body part B. However, as in the illustrated example or as in other known examples, each stretchable region may be located in each part.

The outer member 20 described above can be manufactured using techniques disclosed in JP H04-028363 A and JP H11-332913 A, for example. In addition, the curved elastic members 26, 27 can be preferably cut and made discontinuous on the inner member 10 by cutting methods disclosed in JP 2002-035029 A, JP 2002-178428 A and JP 2002-273808 A.

Unlike the illustrated example, the curved elastic members 26, 27 may be provided only in either one of the front body part F and the back body part B. Further, when the curved elastic members 26, 27 are provided in both the front body part F and the back body part B, a mode in which a part or a whole of group of the curved elastic members 27 provided in the front body part F and a part or a whole of group of the curved elastic members 26 provided in the back body part B are crossed each other (not shown) may be adopted. However, as the illustrated example, a mode is preferable in which the group of the curved elastic members 27 provided in the front body part F and the group of the curved elastic members 26 provided in the back body part B are separated from each other, without crossing each other, in a middle part of the outer member 20 in the front-back direction LD, and particularly preferable at a position which is slightly closer to the front body part F than to the center of the middle part.

Each of the curved elastic members 26, 27 needs not be entirely curved, and may have a partially linear portion.

Although the stretch rate at the time of fixing the elastic members 24 to 27 can be appropriately determined, for normal adult use, about 160 to 320% for the waist elastic member 24, about 160 to 320% for the under-waist elastic member 25, and about 230 to 320% for the curved elastic members 26, 27.

(Cover Sheet)

As shown also in FIG. 1 and FIG. 4, in order to cover the front and back end portions of the inner member 10 attached on the inner surface of the outer member 20 and in order to prevent leakage from front and back edges of the inner member 10, cover sheets 50 and 60 may be provided. To describe the illustrated embodiment in more detail, the front cover sheet 50 extends from the vicinity of the waist opening of the front body part F to a position which overwraps with the front end portion of the inner member 10, having the same width as the maximum width of the front body part F, whilst the back cover sheet 60 extends from the vicinity of the waist opening of the back body part B to a position which overwraps with the back end portion of the inner member 10, having the same width as the maximum width of the back body part B. Substantially whole surfaces of the cover sheets 50 and 60 may be bonded to surfaces facing them, respectively by a hot melt adhesive or the like. Alternatively, small non-bonded portions may be provided all over (or may be provided only at center parts) in the width direction WD of edge portions of the cover sheets 50 and 60 on the crotch side, respectively. By doing so, the adhesive can be prevented from spilling out, and in addition to this, these non-bonded portions can be provided to float slightly from the top sheet, so that they can be functioned as leak-proof walls, respectively.

As the illustrated embodiment, when the cover sheets 50 and 60 are attached as separate bodies, although there is an advantage that the degree of freedom of material selection increases, there are a disadvantage such as an increase in materials and manufacturing processes. Therefore, it is also possible to form portions equivalent to the above described cover sheets 50 and 60 by extending the folded portion 20C, which is formed by folding the outer member 20 toward the internal surface of the diaper, to a portion overlapping with the inner member 10.

(Dorsal Side Barrier)

As shown in FIG. 1, FIG. 3, FIG. 4 and the like, a dorsal side barrier 70 is provided to be closer to the waist opening than a crotch portion of the back body part B. The dorsal side barrier 70 includes a first blocking position B1 for blocking a movement of excrement toward the back side, and second blocking positions B2 for blocking movements of the excrement toward both sides in the width direction WD. The first blocking position B1 is not particularly limited. However, it is preferable that the first blocking position B1 may be overwrapped with the back end portion of the inner member 10. Specifically, it is more preferable that the first blocking position B1 is between the back end portion of the inner member 10 and the back end portion of the absorber 13. Nonetheless, the first blocking position B1 may be overwrapped with the back end portion of the absorber 13. The second blocking position B2 is not particularly limited. However, it is preferable that the second blocking position B2 extends along the front-back direction LD, passing a vicinity of a side edge 10*e* of the inner member 10 (for example, between a fore end edge 90*e* of the standup gather part 90 and a position which is obtained by a mirror image inversion of the fore end edge 90*e* with respect to the side edge 10*e* of the inner member 10).

The dorsal side barrier 70 includes mainly a barrier sheet 71 having a width wider than a dimension in the width direction of the first blocking position B1 (an interval in the width direction between the second blocking positions B2) and extending from a front side of the first blocking position B1 to a back side thereof, and an elongated barrier elastic member to be discussed later. As the barrier sheet 71, as the illustrated example, a dedicated sheet is provided. Alternatively, the barrier sheet 71 may be formed by extending the cover sheet 60 of the back body part B toward the crotch portion. The material of the barrier sheet 71 is not particularly limited. However, it is desirable that a similar material as that of the gather sheet 95 is used. Nonetheless, a similar material as that of the pressing sheet 20A, back sheet 20B, cover sheet 50 or cover sheet 60 may be used.

The barrier sheet 71 includes a base portion 72 adjacent to the first blocking position B1 on the back side thereof, and a main portion 73 adjacent to the first blocking position B1 on the front side thereof. The base portion 72 is a portion fixed to a top surface of the back body part B (in the illustrated example, a top surface of the cover sheet 60 in the outer member 20). On the other hand, the main portion 73 has both side portions 73*s* adjacent to the second blocking positions B2 on outer sides (both lateral sides) thereof and an intermediate portion 73*m* disposed between the second blocking positions B2. Each of both the side portions 73*s* of the main portion 73 has a first portion 81 extending on the front side of the first blocking position B1, a second portion 82 being folded back toward a top side at a folding position along a front edge of the first portion 81 and extending backward, and a third portion 83 being folded back toward the top side at a folding position along a back edge of the second portion 82 and extending forward. An underside surface of the first portion 81 is fixed to the top surface of the back body part B, an underside surface of the second portion 82 is fixed to a top surface of the first portion 81, and the third portion 83 is unfixed to the second portion 82. The intermediate portion 73*m* of the main portion 73 is unfixed to the top surface of the back body part B (in the illustrated example, a top surface of the cover sheet 60 in the outer member 20 and the top surface of the inner member 10). As illustrated in the drawing, the base portion 72 and the first portion 81 may be fixed to each other by a hot melt adhesive HM1, and the first portion 81 and the second portion 82 may be fixed to each other by a hot melt adhesive HM2. Alternatively, although not shown, material welding of the barrier sheet 71 may be used for the fixing.

In addition, the main portion 73 includes the elongated barrier elastic member 74 provided to extend in the width direction WD from one of the third portions 83 to the other of the third portions 83. In the natural length state, as shown in FIG. 9, the main portion 73 is elastically contracted in the width direction WD together with the barrier elastic member 74. However, the barrier elastic member 74 is not provided so as to extend from a back end portion of one of the third portions 83 to a back end portion of the other of the third portions 83. In the illustrated example, the barrier sheet 71 has a two-layered structure formed integrally by the hot melt adhesive or the like (the dotted pattern regions in cross-sectional views). Then, the barrier elastic member 74 and the like are disposed between these two layers so as to be fixed by the hot melt adhesive or the like. Alternatively, the barrier elastic member 74 and the like may be fixed on either one of the top surface and underside surface of the barrier sheet 71. In a case where the barrier sheet 71 has the two-layered structure, as the illustrated example, single sheet may be folded at a back end (or a front end) thereof. Alternatively, two separate sheets may be stacked. Further, in order to improve a waterproof property and stiffness, a liquid-shielding sheet, which is similar to the liquid impervious sheet 12, may be disposed between the layers of the barrier sheet 71.

The dorsal side barrier 70 has a characteristic folding back structure and a characteristic arrangement of the barrier elastic member 74, as stated above. Thus, in the natural length state, the dorsal side barrier 70 has a structure as shown in FIG. 9. Precisely, in the main portion 73 of the barrier sheet 71, each of both the side portions 73*s* has, as shown in FIG. 9(*b*), a folding back structure extending from the first portion 81 to the second portion 82 and a folding back structure extending from the second portion 82 to the third portion 83, but the intermediate portion 73*m* disposed between both the side portions 73*s* is gradually unfolded to a front side with increasing proximity to a center side in the width direction WD so as to spread completely, as shown in FIG. 9(*c*), (or partway) to the front side at a center portion in the width direction WD (the first status). The reason of this may not be clear, but it is possible to consider as follows: in the natural length state, the intermediate portion 73*m* of the main portion 73 is elastically contracted together with the barrier elastic member 74; here, the intermediate portion 73*m* provided with the barrier elastic member 74 is an unfixed free portion, and the barrier elastic member 74 is provided only in a position separated from a back edge of the third portion 83, thus, the third portion 83 is inclined freely to the center side in the width direction WD as shown in FIG. 9(*a*); incidentally, based on an elastic contraction force of the barrier elastic member 74, a force is applied to the intermediate portion 73*m* of the main portion 73; a component of this force, in a direction along which the intermediate portion of the main portion is folded back in a similar way to both the side portions, becomes smaller due to the third portion inclined freely to the center side in the width direction; in this way, the first status is generated. Additionally, since contraction pleats extending in the front-back direction LD are formed all over the intermediate portion 73*m* of the main portion 73, a stiffness of the main portion becomes higher (which makes it difficult for the main portion to be folded and to be bent in the front-back direction LD). It is considered that this high stiffness also affects the intermediate portion 73*m* of the main portion 73 to be unfolded so as to spread.

On the other hand, for wearing the diaper, as the main portion 73 of the barrier sheet 71 is made to be stretched in the width direction WD together with the barrier elastic member 74, in each of both the side portions 73*s* of the main portion 73, the folding back structure continued from the first portion 81 to the second portion 82 is maintained and the folding back structure continued from the second portion 82 to the third portion 83 is maintained to a certain extent as shown in FIG. 4(*b*). However, in the intermediate portion 73*m* of the main portion 73, a pivot portion, which is located to be closer to a fore end edge of the main portion than an imaginary line extending in the width direction WD so as to pass along a boundary (folding back position) between the first portion 81 and the second portion 82, pivots backward around the imaginary line as indicated by arrows illustrated in FIG. 4(*a*), 4(*c*)(the second status). The reason of this may not be clear either, but it is possible to consider as follows: for wearing the diaper, the barrier elastic member 74 is stretched so as to be closely analogous to a straight line along the width direction WD; based on the elastic contraction force of the barrier elastic member 74, the force is applied to the intermediate portion 73*m* of the main portion 73; the component of this force, in the direction along which the intermediate portion of the main portion is folded back in the similar way to both the side portions, becomes larger due to the barrier elastic member stretched so as to be closely analogous to the straight line along the width direction WD; on the other hand, a folding force hardly applies to the third portion since the third portion is unfixed all over the width direction; in this way, the second status is generated. Incidentally, the degree of the pivoting can be adjusted properly by the arrangement of the barrier elastic member 74 and the like. Depending on the degree of pivoting, the third portion can pivot so as to stand up slightly from the natural length state, the third portion can pivot so as to fall over backward (toward a waist opening) which is opposite to the natural length state, or the like.

As is known from the above mentioned change in the first status and in the second status discussed above, in a worn state where the intermediate portion 73*m* of the main portion 73 is contracted to a certain degree, a pocket-type dorsal side barrier 70 is formed between the intermediate portion 73*m* of the main portion 73 and the top surface of the back body part B so as to open toward the crotch portion, because, the intermediate portion 73*m* of the main portion 73 is unfixed to the top surface of the back body part B, while the base portion 72 located at the back side of the intermediate portion and both the side portions 73*s* located on both the sides of the intermediate portion in the main portion 73 are fixed to the top surface of the back body part B directly or indirectly. As a result, when excrement reaches the pocket, the movement of the excrement toward the back side and the movements of the excrement toward both the sides can be prevented by the pocket. It is preferable that the standup portion 94 of the standup gather part 90 is configured so as to be located within the pocket as shown in FIG. 13 and FIG. 14, because it becomes easier for the pocket of the dorsal side barrier 70 to open due to a standup force of the standup gather part 90. However, the fallen portion 93 of the standup gather part 90 may be configured so as to be located within the pocket of the dorsal side barrier 70, or the back end of the inner member 10 may be configured so as to be located on a front side of the pocket of the dorsal side barrier 70.

As stated above, in the present underpants-type disposable diaper, the dorsal side barrier 70 changes as in the above mentioned first status, as in the second status, and as in the worn state. Thus, when the diaper is used, the dorsal side barrier 70 can stand up automatically, so that a case where the diaper is used while the dorsal side barrier 70 is flattened is less likely to occur. Now, a case where a pad-type absorbent article is laid on the internal surface of the present underpants-type disposable diaper is considered. Before the underpants-type disposable diaper is worn, the dorsal side barrier of the diaper is in the first status as shown in FIG. 10(*a*). Then, when the wearer's legs are passing through the leg opening openings for wearing the diaper as shown in FIG. 11, since the wearer's legs are outstretched to a certain extent, the lower torso region of the outer member 20 is stretched in the width direction as indicated by arrows in FIG. 11. The main portion 73 of the barrier sheet 71 is thereby stretched in the width direction WD together with the barrier elastic member 74. Accordingly, in the intermediate portion 73*m* of the main portion 73, as shown in FIG. 10(*b*), the above mentioned pivot portion pivots to be turned up. Therefore, in such a situation, as shown in FIG. 10(*c*), the pad-type absorbent article 30 may be laid on the internal surface of the diaper by locating a back end portion of the pad-type absorbent article 30 according to a position at which the dorsal side barrier is turned up. Lastly, when this underpants-type disposable wearing article is pulled up to the worn state, as shown in FIG. 10(*d*), the dorsal side barrier 70 is returned to a state similar to the natural length state such that the dorsal side barrier 70 can cover the back end portion of the pad-type absorbent article. On the other hand, for wearing the diaper, if a dorsal side barrier 170 does not stand automatically as shown in FIG. 16(*a*), unless a user stands manually the dorsal side barrier 170 and insert the pad-type absorbent article 30 under the dorsal side barrier 170, the dorsal side barrier 170 cannot be functioned appropriately for the pad-type absorbent article 30, and additionally, there is a concern that by mistake, the pad-type absorbent article 30 is laid on the dorsal side barrier 170, which is flatly laid down, as shown in FIG. 16(*b*).

By determining appropriately dimensions of each portion of the barrier sheet 71 and a stretch rate of the third portion 83, to what degree the intermediate portion 73*m* of the main portion 73 pivots may be adjusted by to what degree the third portion 83 is stretched. For example, the following dimensions and stretch rate can be listed.

a dimension in the width direction WD of the intermediate portion 73*m* of the main portion 73: 180 to 200 mm, a dimension L2 in the front-back direction LD of the second portion 82: 5 to 25 mm, a dimension L3 in the front-back direction LD of the third portion 83: 10 to 35 mm, a stretch rate in the width direction WD of the third portion 83 at a maximum stretch: 180 to 280%, and an interval 74D in the front-back direction LD between a back edge of the third portion 83 and the barrier elastic member 74: 3 to 20 mm.

In this case, under a situation where the third portion is stretched at a stretch rate being 0.4 times or more the stretch rate at the maximum stretch, the above mentioned pivot portion may pivot about 90 degrees or more with respect to the top surface of the back body part B, then, reaching a situation where the third portion is stretched at a stretch rate being 0.6 times or more the stretch rate at the maximum stretch, the pivot portion may fall down on the back side (the waist opening side) like a situation at a maximum stretch as shown in FIG. 4. Incidentally, conditions for such behaviors are not limited thereto.

It is preferable that, in addition to the elongated barrier elastic member 74, an elongated shaping elastic member 75, which is provided to extend all over the width direction WD of the dorsal side barrier 70 through at least one of the first portion 81, the second portion 82 and the base portion 72, is provided, and the dorsal side barrier is elastically contracted in the width direction WD together with the elongated shaping elastic member 75 in the natural length state, because a shape of the dorsal side barrier may become organized, and in addition to this, it becomes easier for the intermediate portion 73*m* to be unfolded so as to spread in the natural length state. In the illustrated example, one elongated shaping elastic member 75 is provided to extend in the width direction WD from one of the second portions 82 to the other of the second portions 82 in the main portion 73. Further, three elongated shaping elastic members 75 are provided to extend in the width direction WD across both the side portions 73*s* of the base portion 72. However, the shaping elastic member 75 extending through the first portion 81 is not provided. When a plurality of shaping elastic members 75 are provided to extend through a portion selected from the base portion 72, the first portion 81 and the second portion 82, an interval in the front-back direction LD of the shaping elastic members may be about 3 to 7 mm.

In the underpants-type disposable diaper according to the present example, the outer member 20 has, in a front-back direction LD range including the side seal portions 21, a lower torso stretchable region (a stretchable region formed by the waist elastic member 24 and the under-waist elastic members 25), which is elastically contracted in the width direction WD, and a non-stretchable region, which is located in a middle part in the width direction WD of a range overlapping with the absorber 13. In this case, it is preferable that the base portion 72 of the barrier sheet 71 is fixed to a portion, which is adjacent to the absorber 13 at a back end on the waist opening side thereof in the lower torso stretchable region, so that the base portion is configured so as to be stretchable together with the lower torso stretchable region, because the shape of the dorsal side barrier 70 may be arranged. In addition, in the natural length state, the lower torso stretchable region is elastically contracted in the width direction WD, but the non-stretchable region is not contracted. Accordingly, as the position of a portion including the dorsal side barrier 70 is closer to the front side, contraction in the width direction WD of the portion becomes smaller such that the dorsal side barrier 70 becomes fan-shaped, as shown in FIG. 9(*a*). As a result, it may become easier for the intermediate portion 73*m* to be unfolded so as to spread in the natural length state.

The barrier sheet 71 may have the same color or the same pattern between the top surface and the underside surface thereof. However, it is preferable that in the barrier sheet 71, at least in the intermediate portion 73*m* of the main portion 73 (more preferably the whole main portion 73), a color of the top surface thereof is different from a color of the underside surface thereof, respectively, because the user can easily recognize automatic deformation (change from the first status shown in FIG. 9(*a*) to the second status shown in FIG. 15) of the above mentioned dorsal side barrier 70. Additionally, there is another advantage as follows. Precisely, when the present underpants-type disposable diaper is used together with the pad-type absorbent article 30, which is to be laid on an internal surface of the present diaper, it becomes easier for the user to recognize an appropriate position for laying the pad-type absorbent article 30. The illustrated example assumes a mode where although a first surface is hidden underside in the first status while the first surface is exposed to the top side in the second status, then, the first surface is colored while a second surface (a reverse side of the first surface) is not colored. In contrast, a mode where the second surface is colored while the first surface is not colored can be adopted. Alternatively, also a mode where the color of the first surface is different from the color of the second surface can be adopted. The coloring can be performed by an appropriate technique such as printing on the barrier sheet 71 and spun-dyeing of the material of the barrier sheet 71. Instead of coloring, a pattern may be printed, a pattern may be added to the barrier sheet 71 by embossing, or a character representation, a mark representation, and the like may be added.

<Description of Terms in Specification>

In a case where the following terms are used in the specification, these terms have the following meanings unless otherwise specified in the specification.

The "front-back direction" refers to the direction shown by the reference sign LD (longitudinal direction) in the figures, whereas the "width direction" refers to the direction shown by the reference sign WD (right-left direction) in the figures, and the front-back direction and the width direction are orthogonal to each other.

The "spread state" refers to the state in which an article is spread flatly without contraction or slack.

The "stretch rate" refers to a value when the natural length is 100%. For example, the stretch rate of 200% has the same meaning as the elongation ratio of 2.

The "basis weight" is measured as below. A sample or a test piece is pre-dried, and then is left in a test room or a device in a standard state (temperature 23±1° C., relative humidity 50±2% in a test location), and is put in a constant weight state. Pre-drying refers to setting the weight of the sample or the test piece to a constant weight in an environment in which temperature is 100° C. Incidentally, pre-drying is unnecessary for a fiber having an official moisture regain of 0.0%. A sample having dimensions of 100 mm×100 mm is cut off from the test piece in the constant weight state using a sampling template (100 mm×100 mm). A weight of the sample is measured and multiplied by 100 to calculate a weight per square meter, and the weight is set to the basis weight.

The "thickness" is automatically measured under the condition of load: 0.098 N/cm$^2$ and pressure area: 2 cm 2 using an automatic thickness meter (KES-G5 handy compression tester).

When there is no description about an environmental condition in a test or measurement, it is presumed that the test or measurement is performed in a test room or a device in a standard state (temperature 23±1° C., relative humidity 50±2% in a test location).

Dimensions of each portion refer to dimensions in a spread state rather than the natural length state unless otherwise stated.

INDUSTRIAL APPLICABILITY

The present invention can be used for general underpants-type disposable wearing articles such as underpants-type disposable diaper covers, and underpants-type sanitary napkins, in addition to the underpants-type disposable diapers as in the above example.

REFERENCE SIGNS LIST

10 Inner member
11 Top sheet
12 Liquid impervious sheet
13 Absorber
14 Wrapping sheet
20 Outer member
20C Folded portion
21 Side seal portion
24 Waist elastic member
25 Under-waist elastic member
26, 27 Curved elastic member
26 Dorsal side curved elastic member
27 Ventral side curved elastic member
29 Around-leg line
90 Standup gather part
91 Gather fixed portion
92 Main unit section
93 Fallen portion
94 Standup portion
95 Gather sheet
96 Gather elastic member
F Front body part
B Back body part
LD Front-back direction
WD Width direction
70 Dorsal side barrier
71 Barrier sheet
72 Base portion
73 Main portion
73*s* Both side portions
73*m* Intermediate portion
74 Barrier elastic member
75 Shaping elastic member
81 First portion
82 Second portion
83 Third portion
B1 First blocking position
B2 Second blocking position
Pad-type absorbent article

The invention claimed is:

1. An underpants-type disposable wearing article comprising an integrated outer member provided to extend from a front body part to a back body part or outer members separately provided for the front body part and the back body part, an inner member attached to a middle part of the outer member in a width direction and provided to extend from the front body part to the back body part, side seal portions in which both side portions of the outer member in the front body part and both side portions of the outer member in the back body part are bonded to each other, respectively, a waist opening and a pair of right and left leg opening portions, and a dorsal side barrier provided to be closer to the waist opening than a crotch portion in the back body part, wherein the dorsal side barrier includes a first blocking position for blocking a movement of excrement toward a back side, and second blocking positions for blocking movements of the excrement toward both sides in the width direction, the dorsal side barrier includes a barrier sheet having a width wider than that of the first blocking position and extending from a front side of the first blocking position to the back side thereof, the barrier sheet includes a base portion adjacent to the first blocking position on the back side thereof, and a main portion adjacent to the first blocking position on the front side thereof, the base portion is fixed to a top surface of the back body part, the main portion has both side portions adjacent to the second blocking positions on outer sides thereof and an intermediate portion disposed between the second blocking positions, each of both the side portions of the main portion has a first portion extending on the front side of the first blocking position, a second portion being folded back toward a top side at a folding position along a front edge of the first portion and extending backward, and a third portion being folded back toward the top side at a folding position along a back edge of the second portion and extending forward, an underside surface of the first portion is fixed to the top surface of the back body part, an underside surface of the second portion is fixed to a top surface of the first portion, and the third portion is unfixed to the second portion, the intermediate portion of the main portion is unfixed to the top surface of the back body part, an elongated barrier elastic member is provided to extend in the width direction from one of the third portions to the other of the third portions in the main portion, a back end portion of the third portion is free of the elongated barrier elastic member, and the main portion is elastically contracted in the width direction together with the elongated barrier elastic member in a natural length state.

2. The underpants-type disposable wearing article according to claim 1, wherein the intermediate portion of the main portion has a dimension in the width direction of 180 to 200 mm, the second portion has a dimension in a front-back direction of 5 to 25 mm, the third portion has a dimension in the front-back direction of 10 to 35 mm, the third portion has a stretch rate in the width direction at a maximum stretch of 180 to 280%, and an interval in the front-back direction between a back edge of the third portion and the elongated barrier elastic member is 3 to 20 mm.

3. The underpants-type disposable wearing article according to claim 1, further comprising at least one elongated shaping elastic member selected from an elongated shaping elastic member provided to extend in the width direction from one of the second portions to the other of the second portions in the main portion, an elongated shaping elastic member provided to extend in the width direction from one of the first portions to the other of the first portions in the main portion, and an elongated shaping elastic member provided to extend in the width direction across both side portions of the base portion, wherein the main portion is elastically contracted in the width direction together with the selected at least one elongated shaping elastic member in the natural length state.

4. The underpants-type disposable wearing article according to claim 1, wherein the inner member has an absorber provided in a range including the crotch portion, the outer member has, in a front-back direction range including the side seal portions, a lower torso stretchable region, which is elastically contracted in the width direction, and a non-stretchable region, which is located in a middle part of a range overlapping with the absorber in the width direction, the lower torso stretchable region has a portion, which is adjacent to the absorber at a back end on the waist opening side thereof, and the base portion of the barrier sheet is fixed to the portion, which is adjacent to the absorber at the back end on the waist opening side thereof, to be stretchable together with the lower torso stretchable region.

5. The disposable wearing article according to claim 1, wherein at least in the intermediate portion of the main portion in the barrier sheet, a color, a pattern or a representation of a top surface thereof is different from a color, a pattern or a representation of an underside surface thereof, respectively.

6. The underpants-type disposable wearing article according to claim 2, further comprising at least one elongated shaping elastic member selected from an elongated shaping elastic member provided to extend in the width direction from one of the second portions to the other of the second portions in the main portion, an elongated shaping elastic member provided to extend in the width direction from one of the first portions to the other of the first portions in the main portion, and an elongated shaping elastic member provided to extend in the width direction across both side portions of the base portion, wherein the main portion is elastically contracted in the width direction together with the selected at least one elongated shaping elastic member in the natural length state.

7. The underpants-type disposable wearing article according to claim 2, wherein the inner member has an absorber provided in a range including the crotch portion, the outer member has, in a front-back direction range including the side seal portions, a lower torso stretchable region, which is elastically contracted in the width direction, and a non-stretchable region, which is located in a middle part of a range overlapping with the absorber in the width direction, the lower torso stretchable region has a portion, which is adjacent to the absorber at a back end on the waist opening side thereof, and the base portion of the barrier sheet is fixed to the portion, which is adjacent to the absorber at the back end on the waist opening side thereof, to be stretchable together with the lower torso stretchable region.

8. The underpants-type disposable wearing article according to claim 3, wherein the inner member has an absorber provided in a range including the crotch portion, the outer member has, in a front-back direction range including the side seal portions, a lower torso stretchable region, which is elastically contracted in the width direction, and a non-stretchable region, which is located in a middle part of a range overlapping with the absorber in the width direction, the lower torso stretchable region has a portion, which is adjacent to the absorber at a back end on the waist opening side thereof, and the base portion of the barrier sheet is fixed to the portion, which is adjacent to the absorber at the back end on the waist opening side thereof, to be stretchable together with the lower torso stretchable region.

9. The disposable wearing article according to claim 2, wherein at least in the intermediate portion of the main portion in the barrier sheet, a color, a pattern or a representation of a top surface thereof is different from a color, a pattern or a representation of an underside surface thereof, respectively.

10. The disposable wearing article according to claim 3, wherein at least in the intermediate portion of the main portion in the barrier sheet, a color, a pattern or a representation of a top surface thereof is different from a color, a pattern or a representation of an underside surface thereof, respectively.

11. The disposable wearing article according to claim 4, wherein at least in the intermediate portion of the main portion in the barrier sheet, a color, a pattern or a representation of a top surface thereof is different from a color, a pattern or a representation of an underside surface thereof, respectively.

* * * * *